United States Patent
Rao et al.

(10) Patent No.: US 7,205,393 B2
(45) Date of Patent: Apr. 17, 2007

(54) PROCESS FOR THE ISOLATION AND PURIFICATION OF A GLYCOPROTEIN AVIDIN

(75) Inventors: Mukkavilli Venkata Subba Rao, New Delhi (IN); Munishwar Nath Gupta, New Delhi (IN); Ipsita Roy, New Delhi (IN)

(73) Assignee: Indian Institute of Technology, New Delhi (IN)

( * ) Notice: Subject to any disclaimer, the term of this patent is extended or adjusted under 35 U.S.C. 154(b) by 538 days.

(21) Appl. No.: 10/399,118

(22) PCT Filed: Aug. 2, 2002

(86) PCT No.: PCT/IB02/03044

§ 371 (c)(1),
(2), (4) Date: Sep. 22, 2003

(87) PCT Pub. No.: WO03/099035

PCT Pub. Date: Dec. 4, 2003

(65) Prior Publication Data

US 2004/0063919 A1  Apr. 1, 2004

(51) Int. Cl.
*C07K 1/14* (2006.01)
*C07K 14/465* (2006.01)

(52) U.S. Cl. .............................. 530/412; 530/395
(58) Field of Classification Search .................. None
See application file for complete search history.

(56) References Cited

U.S. PATENT DOCUMENTS 3,515,643 A   6/1970   Ghielmetti et al. ............ 195/66
4,966,851 A  10/1990   Durance et al. ............. 435/206

FOREIGN PATENT DOCUMENTS

WO   WO 00/27814  *  5/2000

OTHER PUBLICATIONS

Gallop et al., How to Dye Cloth, Science, Technology, and Society, Yale-New Haven Teachers Institute, 1987, vol. VI, pp. 1-12.*
Melamed et al., Avidin: Purification and Composition, Biochem. J., 1963, vol. 89, pp. 591-599.*

Green N M, "AVIDIN", in *Advances in Protein Chemistry, Academic Press*, New York, NY, US, ISSN: 0065-3233, p. 87-88,125 (1975).
Green N M et al, "The Properties of Subunits of AVIDIN Coupled to Sepharose", *Biochemical Journal*, 133(4):687-700 (1973).
Durance TD, Nakai S "Simultaneous isolation of avidin and lysozyme from egg albumen", *Journal of Food Science*, 53(4):1096-1102 (1988).
DATABASE WPI "Avidin elution—comprises absorption of basic protein on cation exchange resin", AN 1987-040958 & JP 62 000500 A (QP CORP), abstract (1987).
DATABASE WPI "Avidin isolation from basic protein in egg white—by adsorption in ion exchange bridged dextran, elution with neutral salt soln, etx.", AN 1988-303317 & JP 63 222200 A (EISAI CO LTD), abstract (1988).
DATABASE FSTA 'Online! Cuatrecasas P, Wilchek M "Single-step purification of avidin from egg white by affinity chromatography on biocytin-Sepharose columns", Database accession No. 69-1-03-q0023, abstract (1968).
DATABASE FSTA 'Online! Durance TD, Nakai S "Purification of avidin by cation exchange, gel filtration metal chelate interaction and hydrophobic interaction chromatography", Database accession No. 88-1-11-q0015, abstract (1988).
DATABASE FSTA 'Online! Durance TD "Isolation of avidin and lysozyme from egg albumen", Database accession No. 89-1-06-q0003, abstract (1988).
DATABASE BIOSIS 'Online! Piskarev Ve et al, "A novel preparative method for the isolation of avidin and riboflavin-binding glycoprotein from chicken egg-white by the use of high-performance liquid chromatography", Database accession No. PREV199089125572, abstract (1990).

* cited by examiner

*Primary Examiner*—Robert A. Wax
(74) *Attorney, Agent, or Firm*—Drinker Biddle & Reath LLP; Daniel A. Monaco

(57) ABSTRACT

The present invention provides a process for the preparation of Avidin having a high purity of 98% from egg white, the said process comprising lyophilizing the homogenized egg white with buffer followed by equilibrating the lyophilized material with cation exchanger for an hour at a temperature range of 20° to 30° C.; filtering the mixture to obtain a filtrate and matrix residue; washing the matrix twice with buffer; separating the washings to obtain washed matrix; adding 0.01 M dye in buffer to the washed matrix; equilibrated for an hour at an ambient temperature; separating the supernatant; adding acetic acid to supernatant and dialysing the solution till it is decolorised to obtain pure Avidin.

11 Claims, No Drawings

PROCESS FOR THE ISOLATION AND PURIFICATION OF A GLYCOPROTEIN AVIDIN

TECHNICAL FIELD

The present invention provides an economical and an easily operable process for the preparation of "Avidin" a glycoprotein from egg white using cation exchanger and HABA (4'-Hydroxyazobenzene-2-carboxylic acid) as a selective eluant.

BACKGROUND ART

Avidin is a glycoprotein, which occurs in egg white and is well known because of its property of binding to biotin, with an association constant of $10^{15}$ $M^{-1}$, the highest known for a bioaffinity pair.

Eatkin et al (1940) and Pennington et al. (1942) reports presence of Avidin and isolation in crude form. Conrat et al. (1952) reports very tedious and multi-step process for the isolation of Avidin by involving salt precipitation and adsorption on Bentonite. The above references are pertaining to early days when Avidin was not even characterized at the molecular level.

N. M. Green (1965) screened several anionic dyes for studying binding to Avidin and examined spectroscopically. The most striking results were obtained by using 4'-hydroxyazobenzene-2-carboxylic acid (HABA). Green et al. (1970) describe a multi-step process for the isolation of Avidin involving considerable amount of time. Bayer and Wilchek, (1974) used affinity chromatography on biocytin (ε-N-biotinyl-L-lysine)-linked matrices for the purification of Avidin. Since the association constant with biocytin is very high, 6-M guanidine hydrochloride of pH 1.5 was used for elution. This resulted in poor and irreproducible results. Wilchek and Bayer, (1988) have described Avidin in enzyme-linked immunosorbent assay (ELISA), immunochemical staining, electron microscopy and affinity chromatography.

U.S. Pat. No. 4,966,851 describes the isolation of Avidin using weakly acidic ion-exchanger resin from egg-white by employing stepwise elution with buffer to obtain Avidin having a very low purity of about 12%. Thus, the process leads to non-specific recovery of target protein.

All the prior art processes described earlier involve either multi-step isolation or poor purity of Avidin. The present invention describes a quick, economical, efficient and a single step process for the isolation of Avidin from egg white. Also, the present process has a distinct feature of HABA being used as an eluant to carry out desorption of Avidin from the solid matrix cation exchanger used in the isolation process in comparison to the prior art processes wherein HABA has been always covalently bonded to the solid matrix and the covalently bonded conjugate is in turn used in the process for the isolation of Avidin.

OBJECTS OF THE INVENTION

The main object of the invention is to provide a process for the isolation and purification of Avidin from egg white in a single step.

Another object of the invention is to develop economical and easily operable process for the isolation and purification of Avidin.

Still another object of the invention provides a process of obtaining high purity Avidin from egg white.

Still another object of the invention is to provide a method wherein cation exchanger used can be recycled several times in the process.

Still another object of the invention is to provide a process wherein covalent binding of HABA is not encountered with the cation exchanger used.

In yet another objective of the invention is to develop commercially feasible process for the isolation of Avidin from egg white.

One more objective of the invention is to develop a process wherein some of the raw materials used are recycled.

SUMMARY OF THE INVENTION

Accordingly, the present invention provides an economical and easily operable process for the preparation of Avidin having high purity from egg white.

DETAILED DESCRIPTION OF THE INVENTION

In accordance to the objectives of the invention, the present invention provide a process for the preparation of Avidin having a high purity of 98% from egg white, the said process comprising steps of:
a) homogenizing egg white with buffer,
b) lyophilizing homogenized solution of step (a) to obtain a solid material,
c) dissolving solid egg white in buffer,
d) adding solution of step (c) to equilibrated cation exchanger incubation for an hour at temperature range of 20° to 30° C.,
e) filtering the mixture of step (d) to obtain a filtrate and matrix residue,
f) washing matrix residue of step (e) twice with buffer, removing the washing to obtain washed matrix,
g) adding 0.01 M dye in buffer to the washed matrix of step (f) and equilibrated for an hour in orbital shaker at an ambient temperature;
h) removing the supernatant of step (g),
i) adding acetic acid to supernatant of step (h), so that final concentration of acetic acid is 0.2 N in the solution,
j) dialysing the solution of step (i) till it is decolorized to obtain pure Avidin In an embodiment, Avidin having a purity of 98% was obtained.

In another embodiment, the Avidin is estimated by conventional calorimetric dye-binding assay.

In still another embodiment, the buffer used is selected from acetate buffer or citrate buffer.

In still another embodiment, the concentration of the buffer used is in the range of 0.05 M to 0.15 M and preferably 0.1 M.

Yet another embodiment, the acetate buffer used has a pH in the range of 5.0 to 6.0 and preferably 5.5.

In another embodiment, the citrate buffer used has a pH in the range of 5.0 to 6.0 and preferably 5.5.

In another embodiment, the dye used is selected from 4'-hydroxyazobenzene-2-carboxylic acid (HABA). 4'-hydroxyazobenzene-4-carboxylic acid and 4'-dimethylaminobenzene-2-carboxylic acid.

In still another embodiment, the solid matrix used for purification is cationic exchanger. In still another embodiment, the cation exchanger used is selected from a group consisting of Streamline SP (Amersham Pharmacia, Sweden), CM cellulose (Whatmann, UK) or CM-Sephadex (Pharmacia, Sweden), SP Sephadex, Seralite SRC1120, Seralite WRC-50 and preferably Streamline SP (Amersham Pharmacia, Sweden). The invention is further illustrated by following examples, which should not be construed to limit the scope of this invention.

EXAMPLE 1

Assay of Avidin and Protein

The amount of Avidin in egg white and various fractions is estimated by the colorimetric dye-binding assay (Green, 1970b). The assay is based on the displacement of HABA from the dye-Avidin complex on the addition of biotin and the consequent decrease in absorption of the test solution at 500 nm. The concentration of Avidin (in mg ml$^{-1}$) was calculated as $0.49 \times \Delta A_{500}$.

The amount of protein is measured by the standard dye-binding assay, using bovine serum albumin as the standard protein.

EXAMPLE 2

Isolation of Avidin from Egg White

The whites of four eggs were separated and homogenized. The homogenized solution was lyophilized to obtain about eight grams of solid material. This was dissolved in 25 ml of 0.1 M acetate buffer, pH 5.5 and used as the crude source of avidin.

EXAMPLE 3

Purification of Avidin on a Cation Exchanger in the Batch Mode

Streamline SP (5 ml) was equilibrated with 50 ml 0.1 M acetate buffer, pH 5.5. After, equilibration, the excess buffer is drained completely and the dissolved egg white (25 ml) is added to the cation exchanger and allowed to equilibrate for one hour at 25° C. The unbound egg white solution is removed and the matrix is washed twice with 50 ml of 0.1 M acetate buffer, pH 5.5. The supernatant and the washings were measured for avidin activity and amount of protein. The excess buffer was then removed and 20 ml of 0.01 M HABA solution (in 0.09 M acetate buffer, pH 5.5) is added to the avidin-bound matrix and the solution allowed to equilibrate for one hour at 25° C. (100 rpm, on an orbital shaker). After one hour, the supernatant is collected. Acetic acid (830 µl of 5 N stock solution) is added to dissociate the complex of HABA and avidin. The solution is dialyzed extensively against the assay buffer till the solution becomes colorless. This solution is then assayed for avidin and amount of protein.

MAIN ADVANTAGES OF THE INVENTION 1) the process is economical and easy to operate for isolating bulk quantity of avidin.
2) the process provides high purity of avidin.
3) provides a process for selective elution of avidin with HABA

The invention claimed is:

1. A process for the isolation and purification of Avidin from egg white, the said process comprising steps of:
 a) homogenizing egg white with a buffer to form a homogenized solution,
 b) lyophilizing the homogenized solution of step (a) to obtain a solid egg white material,
 c) dissolving the solid egg white material in a buffer to form a solution,
 d) adding the solution of step (c) to an equilibrated cation exchanger and incubating for an hour at a temperature range of 20° to 30° C. to give a mixture,
 e) filtering the mixture of step (d) to obtain a filtrate and a matrix residue,
 f) washing the matrix residue of step (e) twice with a buffer to obtain washed matrix,
 g) adding 0.01 M of a dye in a buffer to the washed matrix of step (f) and equilibrating for an hour in an orbital shaker, the dye selected from the group consisting of 4'hydroxyazobenzene-2-carboxylic acid, 4'-hydroxyazobenzene-4-carboxylic acid and 4'-dimethylaminobenzene-2-carboxylic acid,
 h) removing a supernatant after performing the eqilubration of step (g),
 i) adding acetic acid to the supernatant of step (h), to form a solution with a final concentration of acetic acid of 0.2 N, and
 j) dialysing the solution of step (i) until it is decolorised to obtain pure Avidin.

2. A process as claimed in claim 1, wherein in steps (a), (c), (f) and (g) the buffer is selected from group consisting of acetate buffer or citrate buffer.

3. A process of claim 2, wherein the acetate buffer used is prepared by mixing a solution of sodium acetate and acetic acid.

4. A process of claim 2, wherein the citrate buffer is prepared by mixing a solution of sodium citrate and citric acid.

5. A process of claim 3, wherein the acetate buffer has a pH in the range of 5.0 to 6.0.

6. A process of claim 4, wherein the citrate buffer has a pH in the range of 5.0 to 6.0.

7. A process as claimed in any of the preceding claims, wherein the concentration of the buffer is in the range of 0.05 M to 0.15 M.

8. A process of claim 1, wherein the dye is 4'-hydroxvazobenzene-2-carboxylic acid.

9. A process as claimed in claim 8, wherein in step (g) the ionic strengths of the equilibration buffer and a solution of 4'-hydroxyazobenzene-2-carboxylic acid in equilibration buffer used are the same.

10. A process as claimed in claim 1, wherein in step (j) the dialysis is performed at a temperature range of 0° C. to 5° C.

11. A process as claimed in claim 1, wherein in step (j) the Avidin obtained has a purity of 98%.

* * * * *